Aug. 21, 1973 J. T. IRWIN Plant Pat. 3,389
KALANCHOE PLANT
Filed Feb. 16, 1972
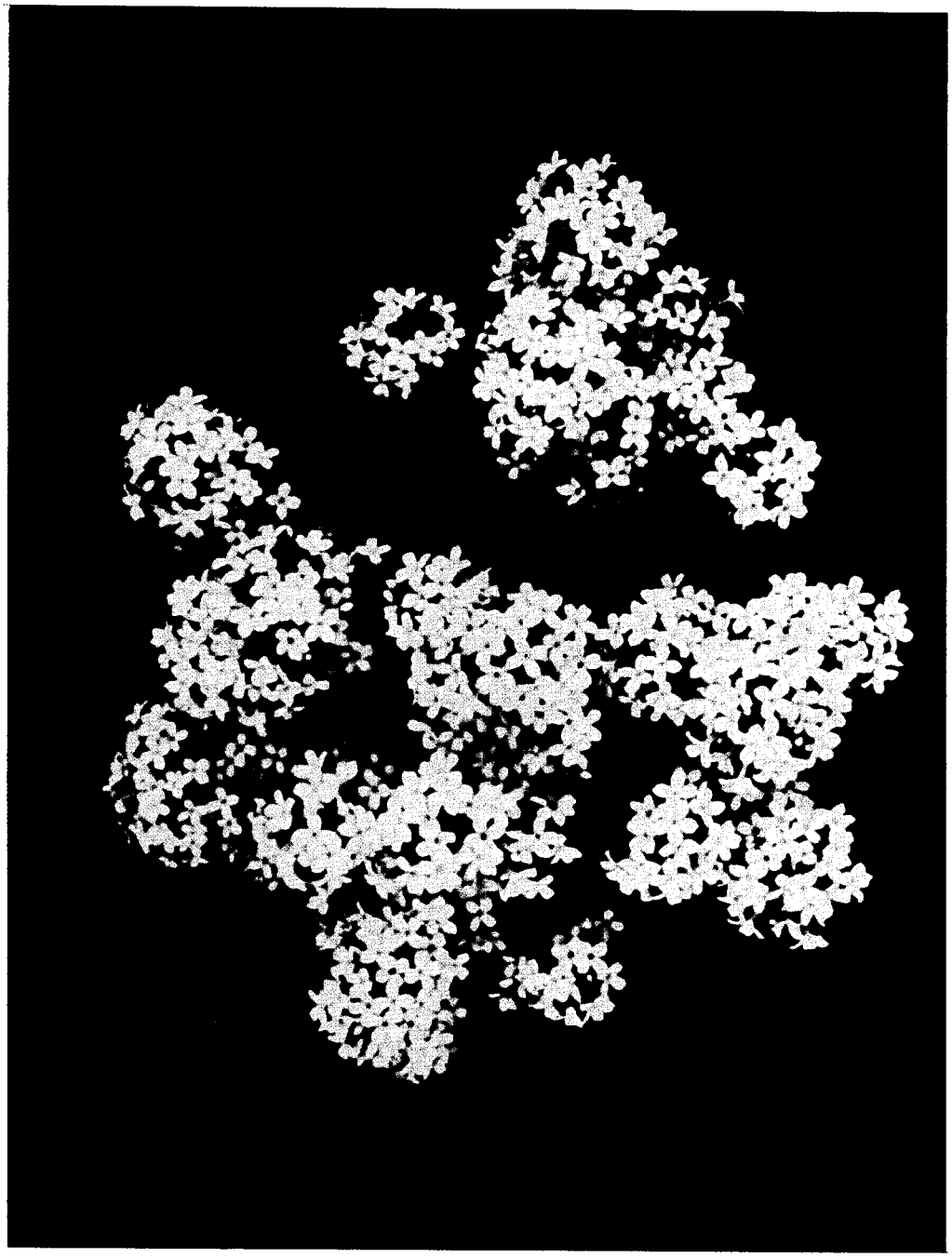

United States Patent Office

Plant Pat. 3,389
Patented Aug. 21, 1973

3,389
KALANCHOE PLANT

James T. Irwin, Canyon, Tex., assignor to
Irwin Greenhouses, Inc., Canyon, Tex.

Filed Feb. 16, 1972, Ser. No. 226,995
Int. Cl. A01h 5/00
U.S. Cl. Plt.—68 1 Claim The present invention relates to a new and distinct variety of kalanchoe plant which was discovered by me as a cultivated sport of the kalanchoe variety known as "Exotic Gold" (patent pending), said discovery having been made by me in one of my commercial greenhouses which I maintain at Canyon, Tex.

At the time of my discovery, I was growing in my greenhouses aforesaid various varities of kalanchoe plants, including a test block of the variety "Exotic Gold" which had previously been discovered and developed by me in my greenhouses located in Randall County, Tex. In the course of these growing and testing operations which were being conducted under my personal supervision and care, my attention was attracted to one particular plant among those of "Exotic Gold" which bore flowers of a distinctive buttercup yellow color, instead of the normal apricot color typical of the flowers of "Exotic Gold." Close inspection of this particular plant showed that it had sported a single branch and flowering stem which bore the buttercup yellow flowers to which my attention had been initially attracted, and I accordingly took steps to carefully preserve the sport and keep it under close observation. In due course, I asexually reproduced the sport in my greenhouses aforesaid by direct rooting of stem tip cuttings taken from the original sport branch. Continued observations and tests of the original sport and its progeny derived therefrom, as indicated in the foregoing, fully confirmed that the buttercup yellow color of the flowers thereof comes true and remains stable as a unique and distinctive kalanchoe flower color, combined with other features which are outstanding, and which, on the whole, represent a unique and commercially valuable new kalanchoe variety which is distinguished from its parent variety, as well as from all other kalanchoe varieties, as evidenced by the following principal characteristics which are outstanding in my new sport:

(1) A highly branched, sturdy, compact and upright habit of growth;

(2) Medium sized, flexible foliage of moss green to fern green color;

(3) A consistent plant height ranging from about 12 to 15 inches tall under greenhouse conditions and a uniform blooming date;

(4) An ability to initiate and develop flower buds under high night temperatures of summer when other varieties fail;

(5) A profuse blooming habit, with the ability to respond to short day treatment, and with consequent capability of year-around flowering;

(6) A distinctive, attractive and uniform buttercup yellow flower color;

(7) Superior resistance to root rot as compared with most other kalanchoe varieties; and (8) Long-lasting qualities as a potted plant.

The accompanying drawing shows a typical specimen plant of my new kalanchoe variety as depicted in bloom and in color as nearly true as it is reasonably possible to make the same in an illustration of this character.

The following is a detailed description of my new kalanchoe variety, with color terminology in accordance with the Exotica Horticultural Color Guide, published by Roehrs Co., of Rutherford, N.J., except where general color terms of ordinary dictionary significance are obvious:

Parentage: Sport of "Exotic Gold" (patent pending).

Propagation: Holds its distinguishing characteristics through succeeding propagations by direct rooting of stem tip cuttings.

Locality where grown and observed: Canyon, Randall County, Tex.

Plant:

*Form.*—Much-branched; upright; compact, consistent height ranging from about 12 to 15 inches tall.

*Growth habit.*—Medium vigorous; sturdy; upright; branching; compact.

*Rooting habit.*—Numerous fibrous roots; roots easily from any part of stem.

*Blooming habit.*—Compound umbel.

*Blooming season.*—Normally about December 8 in Randall County, Tex., but suitable for forcing into bloom at any time of year by manipulating long and short days under suitable greenhouse conditions.

Foliage: Flexible.

*Size.*—Medium.

*Quantity.*—Normal abundance.

*Color.*—New foliage—upper side—Fern Green, Color No. 83−; under side—Moss Green, Color No. 82+. Old foliage—upper side—Fern Green, Color No. 83−; under side—Moss Green, Color No. 82+.

*Shape.*—Oval. Base—from obtuse to acute. Tip—obtuse.

*Texture.*—Upper side—Glossy; smooth; under side—smooth.

*Margin.*—Crenate.

*Aspect.*—Glossy.

Disease resistance: Much more resistant to root rot than most former kalanchoe varieties, as determined by comparison with other varieties grown in greenhouses under the same conditions in Randall County, Tex.

Flowers: Perfect.

*Size.*—About ¾ inch (±⅛ inch) in diameter and about ¾ inch deep; petals about ¼ inch wide and about 11/32 inch long.

*Form.*—Perigynous; section petals united; ovary inferior.

*Color.*—New flowers—upper side of petals—Buttercup Yellow, near Color Nos. 4 to 4+; under side of petals—near Color No. 15+. Old flowers—under side of petals—near Color No. 9.

*Blooming period.*—from about 4 to 5 weeks.

Hardiness: Good; has successfully withstood temperatures as low as 35° F. in central New Mexico, and as high as 105° F. in Canyon, Tex.

General observations: My new kalanchoe variety generally resembles its parent variety "Exotic Gold" except for its flower color which is a unique Buttercup Yellow instead of the Apricot color of the flowers of the parent variety, thereby expanding the color range of kalanchoe flowers as a commercially valuable asset from the standpoint of selective appeal to the public. The full and compact, yet upright habit of growth forms an excellent base for the long-lasting flower heads.

I claim:

1. A new and distinct variety of kalanchoe plant, substantially as herein shown and described, characterized particularly as to novelty by the unique combination of a highly branched, sturdy, compact and upright habit of growth, medium sized, flexible foliage of moss green to fern green color, a consistent plant height ranging from about 12 to 15 inches tall under greenhouse conditions and a uniform blooming date, an ability to initiate and develop flower buds under high night temperatures of summer when other varieties fail, a profuse blooming habit, with the ability to respond to short day treatment, and with consequent capability of year-around flowering, a distinctive, attractive and uniform buttercup yellow flower color, superior resistance to root rot as compared with most other kalanchoe varieties, and long-lasting qualities as a potted plant.

No references cited.

ROBERT E. BAGWILL, Primary Examiner